US011622725B2

(12) United States Patent
Batzer et al.

(10) Patent No.: US 11,622,725 B2
(45) Date of Patent: Apr. 11, 2023

(54) REDUCTION OF MAGNETIC FIELD-INDUCED INTERFERENCES WHEN MEASURING BIOELECTRIC SIGNALS

(71) Applicant: Siemens Healthcare GmbH, Erlangen (DE)

(72) Inventors: Ulrich Batzer, Spardorf (DE); Peter Greif, Pinzberg/Gosberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 273 days.

(21) Appl. No.: 16/874,877

(22) Filed: May 15, 2020

(65) Prior Publication Data

US 2020/0367831 A1 Nov. 26, 2020

(30) Foreign Application Priority Data

May 24, 2019 (DE) .......................... 102019207672.6

(51) Int. Cl.
*A61B 5/00* (2006.01)
*A61B 6/03* (2006.01)
(Continued)

(52) U.S. Cl.
CPC ............ *A61B 5/7203* (2013.01); *A61B 5/318* (2021.01); *A61B 5/369* (2021.01); *A61B 5/389* (2021.01);
(Continued)

(58) Field of Classification Search
CPC ....... A61B 5/7203; A61B 5/318; A61B 5/369; A61B 5/389; A61B 6/032; A61B 6/4417;
(Continued)

(56) References Cited

U.S. PATENT DOCUMENTS

2015/0087959 A1\* 3/2015 Ro ler .................... A61B 5/333
600/407
2015/0094561 A1\* 4/2015 Rey ...................... A61B 5/7225
600/411

(Continued)

FOREIGN PATENT DOCUMENTS

JP 2005319200 A \* 11/2005

*Primary Examiner* — Colin T. Sakamoto
*Assistant Examiner* — Tommy T Ly
(74) *Attorney, Agent, or Firm* — Harness, Dickey & Pierce, P.L.C.

(57) ABSTRACT

A filter method for reducing interferences of a measuring signal, caused by magnetic fields of a rotatable medical imaging system while measuring bioelectric signals in a differential voltage measuring system, the filter method including: capturing a frequency value of a rotation of a gantry of the rotatable medical imaging system; generating a virtual reference signal as a function of the frequency value captured; estimating, via an adaptive signal filter, an amplitude and a constant phase offset of an estimated interference signal, based upon the virtual reference signal generated and a measuring signal; and filtering the measuring signal with the adaptive signal filter by subtracting the estimated interference signal from the measuring signal. A filter apparatus is also described. Furthermore a voltage measuring system is described. Furthermore, a rotating medical imaging system is described.

18 Claims, 3 Drawing Sheets

(51) Int. Cl.
*A61B 6/00* (2006.01)
*A61B 5/318* (2021.01)
*A61B 5/369* (2021.01)
*A61B 5/389* (2021.01)

(52) U.S. Cl.
CPC ............ *A61B 6/032* (2013.01); *A61B 6/4417* (2013.01); *A61B 6/541* (2013.01)

(58) Field of Classification Search
CPC ......... A61B 5/352; A61B 5/355; A61B 5/725; A61B 6/503; A61B 5/7225; A61B 6/54; A61B 5/25; A61B 5/7217; A61B 5/7285; A61B 5/24; A61B 5/398
See application file for complete search history.

(56) References Cited

U.S. PATENT DOCUMENTS

2016/0345844 A1\* 12/2016 McCombie ........... A61B 5/0024
2019/0261927 A1\* 8/2019 Matthiesen ............ A61B 5/282

\* cited by examiner

REDUCTION OF MAGNETIC FIELD-INDUCED INTERFERENCES WHEN MEASURING BIOELECTRIC SIGNALS

PRIORITY STATEMENT

The present application hereby claims priority under 35 U.S.C. § 119 to German patent application number DE 102019207672.6 filed May 24, 2019, the entire contents of which are hereby incorporated herein by reference.

FIELD

Embodiments of the invention generally relate to a filter method for reducing interferences caused by magnetic fields when measuring bioelectric signals in a differential voltage measuring system. Furthermore, embodiments of the invention generally relate to a filter apparatus. Moreover, embodiments of the invention generally relate to a voltage measuring system with such a filter apparatus. Furthermore, embodiments of the invention generally relate to a rotating medical imaging system.

BACKGROUND

Differential voltage measuring systems for measuring bioelectric signals are used for instance in medicine to measure electrocardiograms (EKG), electroencephalograms (EEG) or electromyograms (EMG).

The cited measurements can also be used in combination with medical imaging processes, such as, for instance, computed tomography. For instance, a heart scan or generally an imaging in the chest area can be clocked by an EKG in order to be able to take heart movements or chest movements into account during the imaging. With the cited imaging methods the patient is located in a tubular examination unit, also known as gantry. During the imaging process in a CT system, a system comprising a detector and x-ray source runs around the patient in order to record projection images from all sides. During a magnetization of a larger region of the gantry, with low field strengths of less than 1 mT, on account of the size of the gantry a magnetic field may already result, which penetrates the patient virtually homogeneously and can thus cause interferences in the EKG signal as far as the mV range. The cited interferences are above all affected by the rotation frequency of the gantry. In modern systems this rotation frequency assumes values from 0.25 to 0.33 Hz. The interferences result in specific characteristic features of differential measurements, such as, for instance, the P-wave (pressure wave) or the T-wave of the electrocardiogram, no longer being clearly identifiable.

Figure 1:
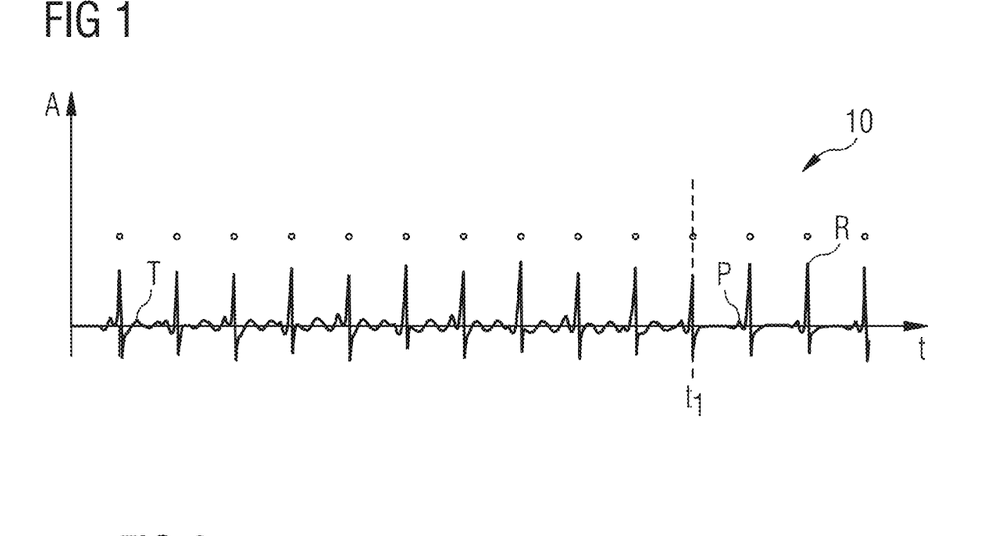
FIG. 1 shows an EKG diagram which is distorted by interference parts which are caused by magnetic fields.

For instance, FIG. 1 shows an electrocardiogram which indicates T-wave-type interferences which occur in a CT system during an image recording. Once the patient has been moved out of the gantry, the interference signal disappears and an EKG signal with a barely measurable T-wave results.

SUMMARY

At least one embodiment of the present invention reduces or even avoids interferences caused by magnetic fields during the measurement of bioelectric signals.

Embodiments are directed to a filter method, a filter apparatus, a differential voltage measuring system and a rotating medical imaging system.

With at least one embodiment of the inventive filter method, a reduction in interference signals is achieved. The relevant interference signals are caused by a magnetic field of a rotating medical imaging system, such as, for instance, a CT system, and occur in a differential voltage measuring system during the measurement of bioelectric signals, if measuring electrodes of the differential voltage measuring system are located in the region of the magnetic field of the rotating medical imaging system. Within the scope of the filter method, a frequency value of a rotation of a gantry of the medical imaging system is firstly captured. The frequency of an interference signal caused by a magnetic field can be determined on the basis of the actuation or the corresponding control signals of the gantry of the rotating medical imaging system. No additional sensors are therefore required for determining this information, since it is predetermined by the controller of the medical imaging system.

The inventive filter apparatus of at least one embodiment has an input interface for receiving a frequency value of a rotation of a gantry of a rotating medical imaging system. Part of the inventive filter apparatus of at least one embodiment is also a reference signal generator unit for generating a virtual reference signal as a function of the captured frequency value. The reference signal generator unit generates a periodic signal, for instance a sinusoidal signal with the captured frequency.

Moreover, the inventive filter apparatus of at least one embodiment also comprises an adaptive filter unit. The adaptive filter unit estimates the missing signal parameters of the interference signal, in particular the amplitude of the interference signal, possibly also the phase offset, and carries out a filtering of the measuring signal, wherein the estimated interference signal is subtracted from the measuring signal. The inventive filter apparatus of at least one embodiment shares the advantages of the inventive filter method of at least one embodiment.

The inventive differential voltage measuring system for measuring bioelectric signals, of at least one embodiment, has the inventive filter apparatus. The inventive differential voltage measuring system of at least one embodiment shares the advantages of the inventive filter apparatus.

The inventive rotating medical imaging system of at least one embodiment, preferably a CT system, has a scan unit, an inventive differential voltage measuring system and a control device for actuating the scan unit as a function of filtered measuring signals of the differential voltage measuring system. The inventive rotating medical system of at least one embodiment can be controlled more accurately on account of the more precise measuring signals of the differential voltage measuring system.

In this regard, at least one embodiment is directed to a corresponding computer program product with a computer program, which can be loaded directly into a storage device of a differential voltage measuring system, with program sections in order to carry out all steps of at least one embodiment of the inventive method when the program is executed in the differential voltage measuring system. One such computer program product can, in addition to the computer program, possibly comprise additional components, such as e.g. a documentation and/or additional components also hardware components, such as e.g. hardware keys (dongles etc.) for the purpose of using the software.

For transport to the differential voltage measuring system and/or for storage at or in the differential voltage measuring system, at least one embodiment is directed to a computer-readable medium, for example, a memory stick, a hard disk or another transportable or firmly installed data carrier can be used on which the program sections of the computer program which are readable and executable by a computer unit of the differential voltage measuring system are stored. For this purpose, the computer unit can have, for example, one or more cooperating microprocessors or the like.

At least one embodiment is directed to a filter method for reducing interferences of a measuring signal, caused by magnetic fields of a rotatable medical imaging system while measuring bioelectric signals in a differential voltage measuring system, the filter method comprising:

capturing a frequency value of a rotation of a gantry of the rotatable medical imaging system;

generating a virtual reference signal as a function of the frequency value captured;

estimating, via an adaptive signal filter, an amplitude and a constant phase offset of an estimated interference signal, based upon the virtual reference signal generated and a measuring signal; and filtering the measuring signal with the adaptive signal filter by subtracting the estimated interference signal from the measuring signal.

At least one embodiment is directed to a filter apparatus, comprising:

an input interface to receive a frequency value of a rotation of a gantry of a medical imaging system;

a reference signal generator to generate a virtual reference signal as a function of the frequency value; and an adaptive filter to estimate an amplitude and a constant phase offset of an estimated interference signal of a measuring signal based upon the reference signal and the measuring signal, and filter the measuring signal by subtracting the estimated interference signal from the measuring signal.

At least one embodiment is directed to a rotating medical imaging system, comprising:

a scan unit;

the differential voltage measuring system of an embodiment; and a control device to activate the scan unit as a function of filtered measuring signals of the differential voltage measuring system.

At least one embodiment is directed to a non-transitory computer program product storing a computer program, directly loadable into a storage device of a differential voltage measuring system, including program sections to carry out the method of an embodiment when the computer program is executed in the differential voltage measuring system.

At least one embodiment is directed to a non-transitory computer-readable medium storing program sections, readable and executable by a computer unit, to carry out the method of an embodiment when the program sections are executed by the computer unit.

BRIEF DESCRIPTION OF THE DRAWINGS

The invention is explained again in more detail below with reference to the appended figures on the basis of example embodiments. In the various figures, the same components are identified with identical reference signs.

The figures are generally not to scale. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

With at least one embodiment of the inventive filter method, a reduction in interference signals is achieved. The relevant interference signals are caused by a magnetic field of a rotating medical imaging system, such as, for instance, a CT system, and occur in a differential voltage measuring system during the measurement of bioelectric signals, if measuring electrodes of the differential voltage measuring system are located in the region of the magnetic field of the rotating medical imaging system. Within the scope of the filter method, a frequency value of a rotation of a gantry of the medical imaging system is firstly captured. The frequency of an interference signal caused by a magnetic field can be determined on the basis of the actuation or the corresponding control signals of the gantry of the rotating medical imaging system. No additional sensors are therefore required for determining this information, since it is predetermined by the controller of the medical imaging system.

Furthermore, a virtual reference signal is generated as a function of the captured frequency value. In other words, the generated virtual reference signal has a frequency with the captured frequency value.

An amplitude and a constant phase offset of an estimated interference signal are then estimated on the basis of the virtual reference signal and the measuring signal by means of an adaptive signal filter. The estimation can be adjusted to the actual measuring signal by means of a comparison with the incoming measuring signal by applying an approximation method, such as, for instance, the least-mean-squares method.

The measuring signal is filtered with the aid of the adaptive signal filter. Here the adaptive signal filter is used as an echo compensator. I.e. the estimated reference signal is subtracted from the measuring signal. In accordance with the invention, the difficulty that a reference signal, which reflects a degree of the interference of the measuring signal, is not available as a measuring signal is circumvented in that one such reference signal is derived or constructed from the control data of the rotating medical imaging system. Therefore not all parameters of the interference signal are known from the control data, however with the aid of the adaptive filter the estimation of the interference signal is significantly simplified or possibly only made possible for the first time by the control data. The fewer parameters of the interference signal which have to be estimated by the adaptive filter, the more quickly an estimation of the interference signal can be completed and thus the more reliable the estimation.

An interference signal generated by magnetic fields can advantageously be removed from the measuring signal so that the signal quality of a differential voltage measurement is improved and weaker characteristics of the measuring signal can also be identified.

The inventive filter apparatus of at least one embodiment has an input interface for receiving a frequency value of a rotation of a gantry of a rotating medical imaging system. Part of the inventive filter apparatus of at least one embodiment is also a reference signal generator unit for generating a virtual reference signal as a function of the captured frequency value. The reference signal generator unit generates a periodic signal, for instance a sinusoidal signal with the captured frequency.

Moreover, the inventive filter apparatus of at least one embodiment also comprises an adaptive filter unit. The adaptive filter unit estimates the missing signal parameters of the interference signal, in particular the amplitude of the interference signal, possibly also the phase offset, and carries out a filtering of the measuring signal, wherein the estimated interference signal is subtracted from the measuring signal. The inventive filter apparatus of at least one embodiment shares the advantages of the inventive filter method of at least one embodiment.

The inventive differential voltage measuring system for measuring bioelectric signals, of at least one embodiment, has the inventive filter apparatus. The inventive differential voltage measuring system of at least one embodiment shares the advantages of the inventive filter apparatus.

The inventive rotating medical imaging system of at least one embodiment, preferably a CT system, has a scan unit, an inventive differential voltage measuring system and a control device for actuating the scan unit as a function of filtered measuring signals of the differential voltage measuring system. The inventive rotating medical system of at least one embodiment can be controlled more accurately on account of the more precise measuring signals of the differential voltage measuring system.

A large part of the previously cited components of the filter apparatus, in particular the reference signal generator unit and the adaptive filter unit, can be realized wholly or partially in the form of software modules in a corresponding differential voltage measuring system. An implementation largely in software has the advantage that even differential voltage measuring systems used previously can be easily retrofitted by a software update in order to operate in an inventive manner.

In this regard, at least one embodiment is directed to a corresponding computer program product with a computer program, which can be loaded directly into a storage device of a differential voltage measuring system, with program sections in order to carry out all steps of at least one embodiment of the inventive method when the program is executed in the differential voltage measuring system. One such computer program product can, in addition to the computer program, possibly comprise additional components, such as e.g. a documentation and/or additional components also hardware components, such as e.g. hardware keys (dongles etc.) for the purpose of using the software.

For transport to the differential voltage measuring system and/or for storage at or in the differential voltage measuring system, at least one embodiment is directed to a computer-readable medium, for example, a memory stick, a hard disk or another transportable or firmly installed data carrier can be used on which the program sections of the computer program which are readable and executable by a computer unit of the differential voltage measuring system are stored. For this purpose, the computer unit can have, for example, one or more cooperating microprocessors or the like.

Further, particularly advantageous embodiments and developments of the invention are given in the claims and in the following description, where the claims in one category of claims can also be developed in a similar way to the claims and passages of the description in another category of claims, and in particular individual features of different example embodiments or variants can also be combined to create new example embodiments or variants.

Preferably, with at least one embodiment of the inventive filter method an adjustment speed of the adaptive filter can be selected as a function of a speed of the movement of the examination couch of the rotating medical imaging system.

For instance, the amplitude can change very quickly with a rapid couch movement. With such a rapid movement, within less than one second the patient is moved out of the scan region to such an extent that his/her abdomen is still present in the gantry but the region in the torso which is relevant to the interference coupling and the measuring cable lie completely outside of the gantry, so that interference no longer occurs in this region. With such a rapid movement, it is therefore important for the transmission function of the adaptive filter and thus also the amplitude of the estimation signal to be adjusted rapidly. On the other hand, with a minimal couch speed, it is important to slow down the adjustment process of the adaptive filter in order to improve the convergence of the adaption process.

The amplitude of the interference signal and thus the amplitude of the reference signal is dependent on the magnetic field strength in the region of the measuring electrodes of the differential voltage measuring system. The magnetic field strength at this point depends on the position relative to the gantry at which the patient is currently located. This position depends on the position of the examination region of the patient and on the current couch position or the position of the patient couch.

In order to capture the entire examination region visually, the patient couch is moved slowly relative to the gantry during the image recording so that the patient position and thus also the position of the measuring electrodes relative to the gantry changes during the measurement. Consequently, the strength of the magnetic field acting on the measuring electrodes and thus also the amplitude of the interference signal changes during the course of the measurement. The knowledge of the patient position can therefore be used to set a start value for an estimation of the amplitude of an estimated interference signal and thus to increase the estimation speed or to improve the reliability of the adaptive filter. The amplitude can also be determined as a function of the size of the patient and of a cable position of a measuring signal cable. Since the size of the patient also influences the cable position and thus the strength of the interfering magnetic field. The position of the cable or of the patient and the size thereof can be captured or determined for instance with the aid of a video camera.

In a special variant of at least one embodiment of the inventive determination method, a magnetic field constant assigned to the system comprising a differential voltage measuring system and medical imaging system is used to determine the amplitude of the reference signal.

The "magnetic field constant" refers to the constant strength of the magnetic field, which is characteristic of the system and is unchangeable over time. A measurement of this constant magnetic field strength is therefore possible in the final inspection before delivering the system.

In the figures, by way of example an EKG measuring system 1 is assumed to be a differential voltage measuring system 1 in order to measure bioelectric signals, here EKG signals. Embodiments of the invention are not restricted hereto, however.

FIG. 1 shows by way of example an EKG diagram which has been recorded with interferences induced by magnetic fields. The interferences result from the rotational movement of magnetized materials, in particular the gantry of a CT system. FIG. 1 plots the amplitude A of an EKG measuring system over time t. With the first 10 cycles of the EKG measuring signal as far as time instant t1, it appears that the EKG would indicate a T-wave T. Wave movements running between individual R-waves nevertheless disappear after the end of the imaging, i.e. after the tenth cycle or time instant t1. As can be seen with the aid of the last three EKG measuring cycles, no T-wave T, but instead a P-wave P and an R-wave R are measured in the EKG without interference. In the case shown in FIG. 1, during the first ten cycles the interference field therefore results in a misinterpretation of the EKG. It would therefore be desirable to suppress or at least reduce the interference part illustrated in FIG. 1.

Figure 2:
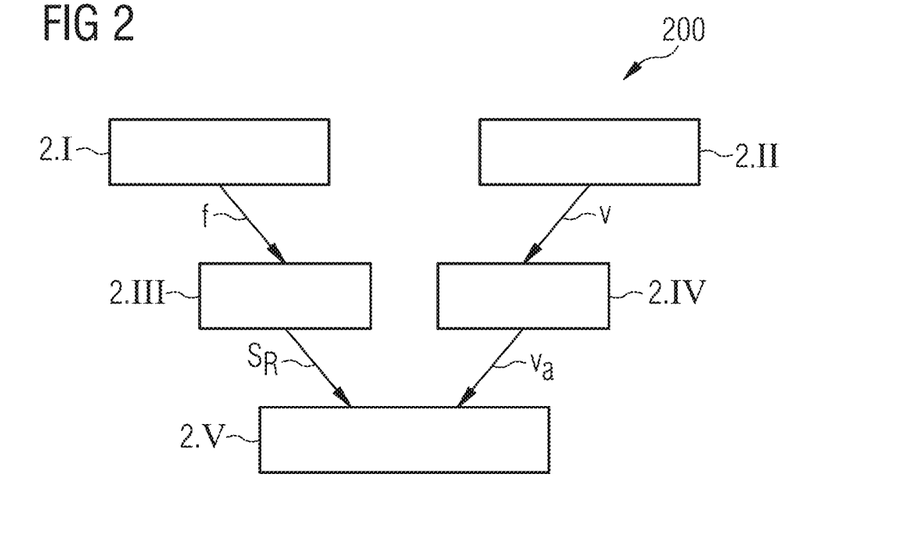
FIG. 2 shows a flow diagram which illustrates a filter method according to an example embodiment of the invention.

FIG. 2 shows a flow chart 200 which illustrates a filter method for reducing interferences caused by magnetic fields of a CT system while measuring bioelectric signals in a differential voltage measuring system. With the method, in step 2.I, a frequency f of a rotation of a gantry of the CT system is firstly determined. For this purpose the frequency f of the rotation of the gantry of a central controller of the CT system is requested. In addition, in step 2.II, the speed v of a couch movement TB is determined during an imaging. This information is also requested by the central controller of the CT system, which regulates the patient position by way of the couch position.

Furthermore, in step 2.III, a virtual reference signal SR is determined on the basis of the determined frequency f of a rotation of a gantry of the CT system. Moreover, in step 2.IV, an adaptation speed vA of the adaptive filter is adjusted on the basis of the determined speed v of a couch movement TB. Finally in step 2.V, an adaptive filtering of the measuring signal S takes place as a function of the determined values f, vA, wherein an interference signal Sest is estimated on the basis of the virtual reference signal SR and the estimated interference signal Sest is subtracted from the measuring signal S. The determination of the correct amplitude A and the phase offset between the measuring signal S and the virtual reference signal SR is carried out by way of adapting the filter function to the measuring signal.

A detection of characteristic features of the measuring signal S can then take place, for instance, like an R-wave detection or a T-wave detection, for instance. The cited steps are constantly repeated during an imaging process or EKG procedure, so that the examination can be monitored continuously.

Figure 3:
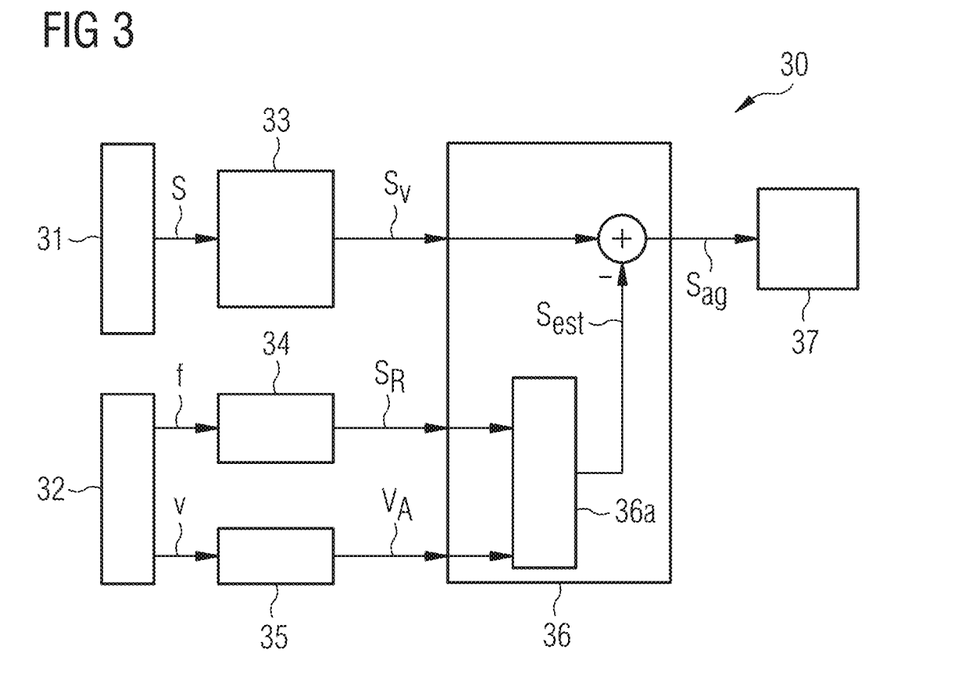
FIG. 3 shows a schematic block diagram of an example embodiment of a filter device according to an example embodiment of the invention.

FIG. 3 shows a schematic block diagram of a filter device 30 according to one example embodiment of the invention. The filter device 30 has a signal input interface 31, which receives a possibly interrupted measuring signal S. In addition, the filter device 30 also comprises a control signal input interface 32, which is connected to a central control device of a CT system and receives information with respect to the rotation frequency f and the speed v of the couch movement of a patient couch of the CT system.

Part of the filter device 30 is also a digital prefilter 33, which performs a bandpass and notch function and generates a prefiltered signal Sv on the basis of the input signal S. A notch filter has a small bandwidth and generates a narrow-band signal. The filter device 30 also has a virtual frequency generator 34, which generates a virtual reference signal SR with a frequency adjusted to the rotation frequency f on the basis of the captured rotation frequency f. Moreover, the filter device 30 also comprises a parameterization unit 35, which defines an adaptation speed vA of a filter function of a filter unit 36 of the filter device 30 on the basis of the speed v of a movement TB of a patient couch.

As a core element the filter device 30 comprises the filter unit 36 with an adaptive filter 36a. The adaptive filter 36a generates a filter function Sest on the basis of the virtual reference signal SR and subtracts this from the prefiltered signal Sv so that a filtered signal Sag is generated. In this special example embodiment the filtered signal Sag is transmitted to an R-wave detector 37 which detects an R-wave in the filtered signal Sag in order to trigger an imaging. A detection of other features, such as for instance the T-wave or P-wave mentioned at the start, is likewise conceivable.

Figure 4:
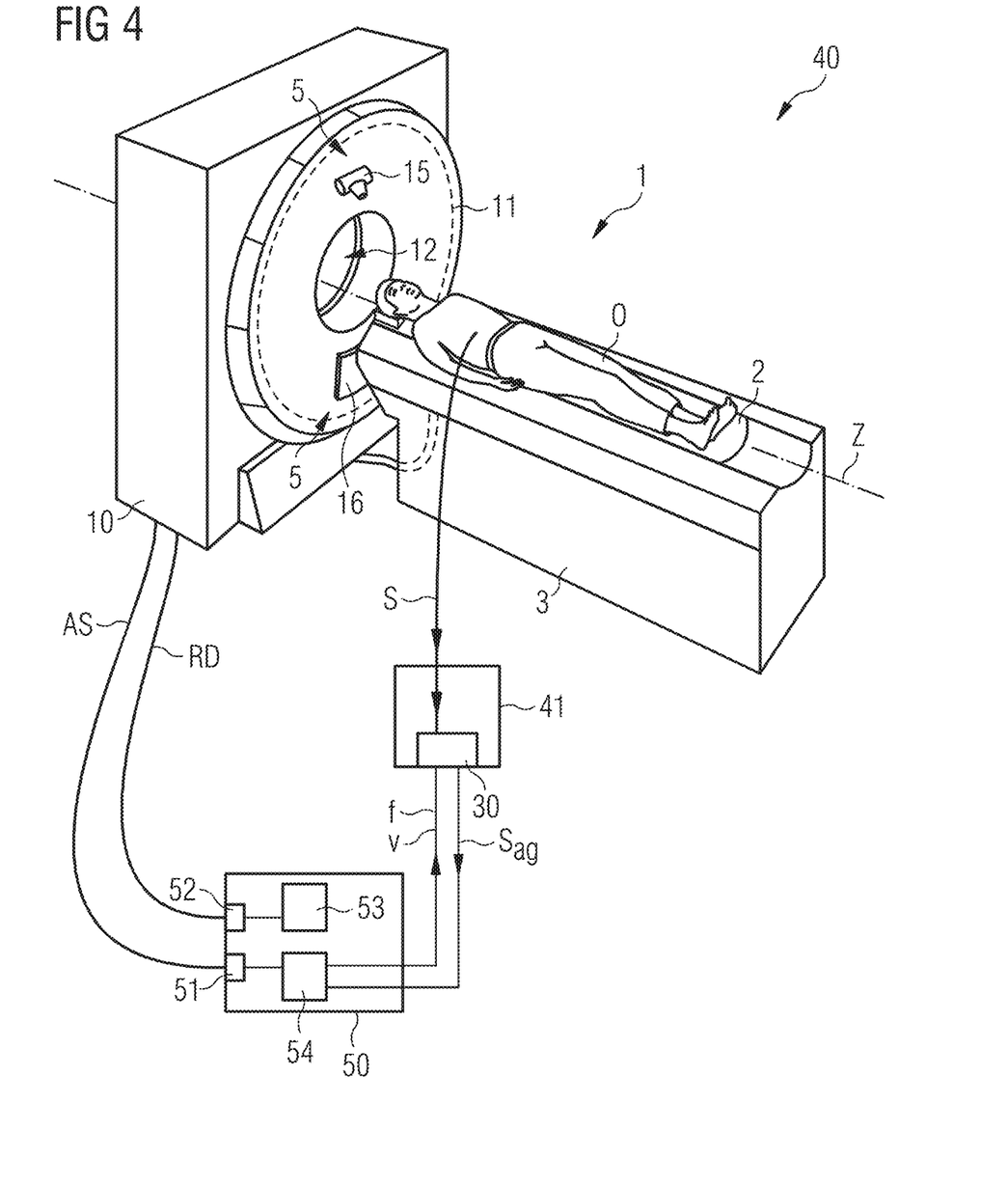
FIG. 4 shows a schematic representation of a CT system according to an example embodiment of the invention.

FIG. 4 shows a CT system 40 with an EKG measuring system 41 with a filter device 30 according to an example embodiment of the invention. The CT system 40 consists here essentially of a conventional scanner 10, in which a projection measurement data acquisition unit 5 with a detector 16 and an x-ray source 15 opposing the detector 16 circulates around a scanning space 12 on a gantry 11. Situated in front of the scanner 10 is a patient positioning device 3 or a patient couch 3, the upper part 2 of which with a patient O situated thereon can be displaced relative to the scanner 10 in order to move the patient O through the scanning space 12 relative to the detector 16. The scanner 10 and the patient couch 3 are activated by a control device 50 from which acquisition control signals AS come via a conventional control interface 51 in order to control the entire system in the conventional manner according to predetermined scan protocols.

In the event of a spiral acquisition, a helical path results due to a movement of the patient O along the z-direction, which corresponds to the system axis z through the scanning space 12, and the simultaneous circulation of the x-ray source 15 for the x-ray source 15 relative to the patient O during the scan. Here the detector 16 always runs in parallel with respect to the x-ray source 15 in order to capture projection measurement data RD which is then used for reconstructing volume image data and/or slice image data.

Similarly, a sequential scanning method can also be carried out, in which a fixed position is approached in the z-direction and then, during a rotation, a partial rotation or a plurality of rotations at the z-position in question, the required projection measurement data RD is captured in order to reconstruct a sectional image at this z-position or in order to reconstruct image data from the projection data of a plurality of z-positions. The inventive filter device is also in principle usable on other CT systems, for example with a detector forming a complete ring. For example, the inventive filter apparatus can also be used on a system with a stationary patient couch and a gantry moving in the z-direction (known as a sliding gantry).

The projection measurement data RD (also referred to in the following as raw data) acquired by the detector 16 is transferred via a raw data interface 52 to the control device 50. This raw data RD is then further processed, possibly following a suitable pre-processing in an image data generation unit 53, which in this example embodiment is realized in the control device 50 in the form of software on a processor. This image data generation unit 53 reconstructs image data BD on the basis of the raw data RD.

The control device 50 also comprises an activation unit 54. From there the units directly involved in the imaging, such as, for instance, the x-ray source 15, the detector 16, the patient couch 3 etc. are then activated by way of activation commands AS. These activation commands AS also comprise the rotation frequency f of the gantry and the couch movement speed v. This data f, v is also transmitted to the EKG measuring system 41. The EKG measuring system 41 receives EKG signals S from the patient O and also comprises a filter apparatus 30, as shown in FIG. 3. The filter apparatus 30 generates a filtered measuring signal Sag on the basis of the EKG measuring signal S and transmits this filtered measuring signal Sag to the control device 50, where the measuring signal Sag is evaluated by the activation unit 54 in order to control the imaging as a function of the heart movement of the patient O.

Finally, it should again be noted that the devices and methods described above in detail are merely example embodiments which can be modified by a person skilled in the art in a wide variety of ways without departing from the scope of the invention. Therefore the differential voltage measuring system not only involves an EKG device, but can instead also involve other medical devices with which bioelectric signals are captured, such as for instance EEGs, EMGs etc. Furthermore, the use of the indefinite article "a" or "an" does not rule out that the relevant features are also available several times. Similarly, the expression "unit" does not preclude this consisting of a plurality of components which can possibly also be spatially distributed.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A filter method for reducing interference in a measuring signal, the interference being caused by a magnetic field of a rotatable medical imaging system while the measuring signal is measured in a differential voltage measuring system, the measuring signal corresponding to a bioelectric signal, the filter method comprising:
    capturing a frequency value of a rotation of a gantry, the gantry being included in the rotatable medical imaging system;
    generating a virtual reference signal having a frequency of the frequency value;
    estimating, via an adaptive signal filter, an amplitude and a constant phase offset of an estimated interference signal, the estimating being based on the virtual reference signal and the measuring signal, the estimating the amplitude of the estimated interference signal being based on a magnetic field constant, and the magnetic field constant being assigned to a system including the differential voltage measuring system; and filtering the measuring signal with the adaptive signal filter by subtracting the estimated interference signal from the measuring signal.

2. The method of claim 1, further comprising:

selecting an adjustment speed of the adaptive signal filter as a function of a speed of movement of an examination couch, the examination couch being included in the rotatable medical imaging system.

3. The method of claim 2, wherein the estimating comprises:

estimating the amplitude of the estimated interference signal based on a position of the examination couch and the magnetic field constant.

4. The method of claim 2, wherein the estimating comprises:

determining the amplitude as a function of at least one of
a size of a patient, or
a cable position of a measuring signal cable.

5. The method of claim 2, wherein the rotatable medical imaging system includes a computed tomography system.

6. The method of claim 1, wherein the estimating comprises:

estimating the amplitude of the estimated interference signal based on a position of an examination couch and the magnetic field constant.

7. The method of claim 6, wherein the estimating comprises:

determining the amplitude as a function of at least one of
a size of a patient on the examination couch, or
a cable position of a measuring signal cable.

8. The method of claim 1, wherein the estimating comprises:

determining the amplitude as a function of at least one of
a size of a patient, or
a cable position of a measuring signal cable.

9. The method of claim 1, wherein the rotatable medical imaging system includes a computed tomography system.

10. The method of claim 1, wherein the capturing the frequency value comprises:

obtaining an actuation signal of the gantry; or
obtaining a control signal corresponding to the actuation signal.

11. The method of claim 1, wherein
the interference is caused by magnetization of the gantry; and
a strength of the magnetic field is less than 1 mT.

12. A non-transitory computer-readable medium storing program sections that, when executed by a computer unit, cause the computer unit to carry out the method of claim 1.

13. A non-transitory computer-readable medium storing a computer program directly loadable into a storage device of a differential voltage measuring system, the computer program including program sections that, when executed in the differential voltage measuring system, cause the differential voltage measuring system to carry out the method of claim 1.

14. A filter apparatus, comprising:

an input interface to receive a frequency value of a rotation of a gantry, the gantry being included in a medical imaging system;

a reference signal generator to generate a virtual reference signal having a frequency of the frequency value; and an adaptive filter to estimate an amplitude and a constant phase offset of an estimated interference signal of a measuring signal, the amplitude and the constant phase offset being estimated based on the virtual reference signal and the measuring signal, the amplitude of the estimated interference signal being estimated based on a magnetic field constant, and the magnetic field constant being assigned to a system including the filter apparatus, and filter the measuring signal by subtracting the estimated interference signal from the measuring signal to obtain a filtered measuring signal.

15. The filter apparatus of claim 14, wherein the input interface is to receive the frequency value by:

obtaining an actuation signal of the gantry; or
obtaining a control signal corresponding to the actuation signal.

16. A differential voltage measuring system for measuring bioelectric signals, the differential voltage measuring system comprising the filter apparatus of claim 14.

17. A rotating medical imaging system, comprising:

a scan unit;
the differential voltage measuring system of claim 16; and
a control device to activate the scan unit as a function of the filtered measuring signal.

18. The rotating medical imaging system of claim 17, wherein the rotating medical imaging system is a CT system.

* * * * *